(12) United States Patent
Safoyan et al.

(10) Patent No.: US 10,994,052 B2
(45) Date of Patent: May 4, 2021

(54) METHOD FOR PRODUCING SUSPENDED FORM OF GROUND DECELLULARIZED EXTRACELLULAR MATRIX

(71) Applicant: LIMITED LIABILITY COMPANY "NEARMEDIC PLUS", Moscow (RU)

(72) Inventors: Ashot Agabegovich Safoyan, Moscow (RU); Anatoly Petrovich Suslov, Moscow (RU); Vladimir Georgievich Nesterenko, Moscow (RU); Sergei Vladimirovich Nesterenko, Moscow (RU); Nina Vladimirovna Kalmykova, Moscow (RU); Ilya Alexandrovich Demyanenko, Moscow (RU); Oleg Vladimirovich Sorokin, Moscow (RU)

(73) Assignee: LIMITED LIABILITY COMPANY "NEARMEDIC PLUS", Moscow (RU)

( * ) Notice: Subject to any disclaimer, the term of this patent is extended or adjusted under 35 U.S.C. 154(b) by 25 days.

(21) Appl. No.: 16/344,714

(22) PCT Filed: Oct. 23, 2017

(86) PCT No.: PCT/RU2017/050111
§ 371 (c)(1),
(2) Date: Apr. 24, 2019

(87) PCT Pub. No.: WO2018/080352
PCT Pub. Date: May 3, 2018

(65) Prior Publication Data
US 2019/0269824 A1 Sep. 5, 2019

(30) Foreign Application Priority Data

Oct. 24, 2016 (RU) .......................... RU2016141560

(51) Int. Cl.
*A61L 27/36* (2006.01)
*A61K 9/10* (2006.01)
(Continued)

(52) U.S. Cl.
CPC ........ *A61L 27/3633* (2013.01); *A61K 9/0019* (2013.01); *A61K 9/10* (2013.01);
(Continued)

(58) Field of Classification Search
CPC .... A61L 27/3633; A61L 2430/40; A61K 9/10
See application file for complete search history.

(56) References Cited

U.S. PATENT DOCUMENTS

| 5,336,616 A | 8/1994 | Livesey et al. |
| 6,933,326 B1 | 8/2005 | Griffey et al. |

FOREIGN PATENT DOCUMENTS

| RU | 2353397 | 10/2008 |
| WO | 99/65470 | 12/1999 |

(Continued)

OTHER PUBLICATIONS

Badylak et al. (Mar. 2011). "Whole-Organ Tissue Engineering: Decellularization and Recellularization of Three-Dimensional Matrix Scaffolds," Annu Rev Biomed Eng 13: 27-53.
Bunyaratavej et al. (Feb. 2001). "Collagen Membranes: A Review," J Periodontol 72(2): 215-229.
Burger et al. (Jul. 2006). "Evaluation of New Prosthetic Meshes for Ventral Hernia Repair," Surgical Endoscopy 20: 1320-1325.
(Continued)

*Primary Examiner* — Timothy P Thomas
(74) *Attorney, Agent, or Firm* — Morrison & Foerster LLP

(57) ABSTRACT

The present invention relates to the field of pharmaceutics and medicine, in particular, to a method for producing a suspended form of ground decellularized extracellular matrix with size-controlled structural components, the suspended form not 5 requiring pre-hydration, and to a product produced by this method, for stimulation of reparative regeneration of tissues.

6 Claims, 5 Drawing Sheets

(51) Int. Cl.

| | | |
|---|---|---|
| *A61P 17/02* | (2006.01) | |
| *A61K 9/00* | (2006.01) | |
| *A61L 15/32* | (2006.01) | |
| *A61L 26/00* | (2006.01) | |
| *A61L 27/20* | (2006.01) | |
| *A61L 27/54* | (2006.01) | |
| *A61L 15/40* | (2006.01) | |
| *A61K 35/34* | (2015.01) | |
| *A61K 35/36* | (2015.01) | |

(52) U.S. Cl.
CPC .............. *A61K 35/34* (2013.01); *A61K 35/36* (2013.01); *A61L 15/32* (2013.01); *A61L 15/40* (2013.01); *A61L 26/009* (2013.01); *A61L 26/0033* (2013.01); *A61L 26/0057* (2013.01); *A61L 27/20* (2013.01); *A61L 27/3691* (2013.01); *A61L 27/54* (2013.01); *A61P 17/02* (2018.01); *A61L 2400/06* (2013.01); *A61L 2430/34* (2013.01); *A61L 2430/40* (2013.01)

(56) References Cited

FOREIGN PATENT DOCUMENTS

| | | |
|---|---|---|
| WO | 2013/163186 | 10/2013 |
| WO | 2014/110269 | 7/2014 |

OTHER PUBLICATIONS

Cornwell et al. (2009). "Extracellular Matrix Biomaterials for Soft Tissue Repair," Clin Podiatr Med Surg 26: 507-523.

Crapo et al. (Apr. 2011). "An Overview of Tissue and Whole Organ Decellularization Processes," Biomaterials 32(12): 23 pages.

International Search Report and Written Opinion dated Feb. 7, 2018, directed to International Application No. PCT/RU2017/050111; 13 pages.

Milstein et al. (Sep. 2005). "Long-term Effects of Micronized Alloderm Injection for Unilateral Vocal Fold Paralysis," Laryngoscope 115: 1691-1696.

Rose et al. (2009). "Effect of a Xenogeneic Urinary Bladder Injectable Bioscaffold on Lameness in Dogs with Osteoarthritis of the Coxofemoral Joint (Hip): A Randomized, Double Blinded Controlled Trial," Intern J Appl Res Vet Med 7(1): 13-22.

Santana et al. (Jan. 2012). "Emulsions Stabilized by Heat-Treated Collagen Fibers," Food Hydrocolloids 26(1): 13-81.

Sclafani et al. (Dec. 2002). "Rejuvenation of the Aging Lip With an Injectable Acellular Dermal Graft (Cymetra)," Arch Facial Plast Surg 4: 252-257.

Seshamani et al. (Feb. 2006). "Cymetra Injections to Treat Leakage Around a Tracheoesophageal Puncture," ORL 68:146-148.

Stevens et al. (Nov. 2005). "Exploring and Engineering the Cell Surface Interface," Science 310: 1135-1138.

Wood et al. (Apr. 2005). "Use of a Particulate Extracellular Matrix Bioscaffold for Treatment of Acquired Urinary Incontinence in Dogs," JAVMA 226(7): 1095-1097.

METHOD FOR PRODUCING SUSPENDED FORM OF GROUND DECELLULARIZED EXTRACELLULAR MATRIX

FIELD OF THE ART

The present invention relates to the field of pharmaceutics and medicine, in particular, to a method for producing a suspended form of ground decellularized extracellular matrix with size-controlled structural components, the suspended form not requiring pre-hydration, and to a product produced by this method, for stimulation of reparative regeneration of tissues.

BACKGROUND

Medical products based on a decellularized (acellular) extracellular matrix currently are widely used in plastic and reconstructive surgery. Moreover, their application in the field of regenerative medicine is continuing to grow. Scientific and practical interest in bioresorbable material of this type is due to its high reparative properties, which largely are provided by the preserved three-dimensional ultrastructure, spatial topology and chemical composition of the extracellular matrix that is present in tissues. Many studies demonstrate the ability of a decellularized extracellular matrix produced by various methods from different sources to promote chemotaxis, cell migration and differentiation, as well as remodelling of autologous tissues (Crapo P. M., Gilbert T. W., Badylak S. F. An overview of tissue and whole organ decellularization processes. Biomaterials. 2011, v. 32, No. 12, pp. 3233-3243).

Most of the decellularized extracellular matrix-based products available in the market are represented by lyophilized plates or membranes intended for use in reparation of defects in the wall of hollow organs (Burger G. W., Halm J. A., Wijsmuller A. R., ten Raa S., Jeekel J. Evaluation of new prosthetic meshes for ventral hernia repair. Surgical endoscopy. 2006, v. 20, No. 8, pp. 1320-1325), regeneration of the bone tissue in dentistry (Bunyaratavej P., Wang H. L. Collagen membranes: a review. Journal of periodontology. 2001, v. 72, No. 2, pp. 215-229.), restoration of ligaments and tendons, and, to a lesser extent, in the treatment of wound skin defects of various etiologies (Cornwell K. G., Landsman A., James K. S. Extracellular matrix biomaterials for soft tissue repair. Clinics in podiatric medicine and surgery. 2009, v. 26, No. 4, pp. 507-523). However, in the surgical treatment of some pathologies, mainly in the field of urology and otolaryngology, as well as in contouring procedures in cosmetology, it is necessary to use injectable forms of biocompatible materials allowing replacement of the lost mechanical function of tissues and activation of reparative processes resulting in formation—of autologous tissues. Also, in the treatment of chronic wounds with mild exudation, it is preferable to use wound dressings that easily fill a wound defect and contain a large amount of moisture. The problem of the development of medical devices combining the above characteristics with the biological properties of a purified extracellular matrix can be largely solved by using ground particles of the matrix, suspended in a liquid phase. Thus, U.S. Pat. No. 6,933,326 B1 and EP 1087756 A1 describe a process for producing a lyophilized ground decellularized extracellular matrix derived from an allogeneic or xenogeneic source, wherein the matrix must be pre-rehydrated before use. Based on the process of this patent, LifeCell Corporation (USA) produces medical device Cymetra®, which is a lyophilized ground allogeneic extracellular matrix of the dermis, packed in a syringe. According to published data, Cymetra® exhibits a therapeutic effect in tracheoesophageal puncture (Seshamani M., Ruiz C., Kasper Schwartz S., Mirza N. Cymetra® injections to treat leakage around a tracheoesophageal puncture. Journal of oto-rhino-laryngology and its related specialities. 2006, v. 68, No. 3, pp. 146-148), laryngoplasty in patients with unilateral vocal cord paralysis (Milstein C. F., Akst L. M., Hicks M. D., Abelson T. I., Strome M. Long-term effects of micronized Alloderm injection for unilateral vocal fold paralysis. Laryngoscope. 2005, v. 115, No. 9, pp. 1691-1696), and lip augmentation (Sclafani A. P., Romo T., Jacono A. A. Rejuvenation of the aging lip with an injectable acellular dermal graft (Cymetra®). Archives of fascial plastic surgery. 2002, v. 4, No. 4, pp. 252-257). In addition, according to the published data a ground purified extracellular matrix of a porcine bladder mixed with a liquid phase directly before injection, was successfully applied in the treatment of urinary incontinence (Wood J. D., Simmons-Byrd A., Spievack A. R., Badylak S. F. Use of a particulate extracellular matrix bioscaffold for treatment of acquired urinary incontinence in dogs. Journal of the American veterinary medical association. 2005, v. 226, No. 7, pp. 1095-1097) and osteoarthritis of the coxofemoral joint in dogs (Rose W., Wood J. D., Simmons-Byrd A., Spievack A. R. Effect of a xenogeneic urinary bladder injectable bioscaffold on lameness in dogs with osteoarthritis of the coxofemoral joint (hip): a randomized, double blinded controlled trial. International journal of applied research in veterinary medicine. 2009, v. 7, No. 1, pp. 13-22).

A significant drawback of the described above approach to the use of a ground decellularized matrix, which significantly limits its application in the treatment methods, is the difficulty of hydrating the material, followed by the preparation of its suspended form for parenteral or external administration. This difficulty is caused mainly by aggregation of the particles of the material and their uneven wetting, which prevents them from being uniformly suspended.

It is known from the published data that a reduction in the size of the structural elements of the matrix on which cells are growing promotes an increase in their viability, as well as acceleration of their migration and differentiation (Stevens M. M., George J. H. Exploring and engineering the cell surface interface. Science. 2005. v.310, No. 5751, pp. 1135-1138). This phenomena is associated with an increase in surface area and, as a consequence, the number of available membrane receptor-binding sites. At the same time, a simple suspending of a ground decellularized matrix in a liquid does not allow to change the dimensional characteristics of the components of the solid dispersed phase, except by varying the particle size of the matrix. This, in turn, makes it very difficult to obtain an injectable bioresorbable material with controlled reparative properties.

Thus, there remains a need for a method for preparing a suspended form of a ground decellularized extracellular matrix with a size-controlled structural components, wherein the form does not require pre-hydration, which can be injected into a desired region without incision, and can easy fill of an open wound of various tissues.

SUMMARY OF THE INVENTION

The problem is solved by the development of a method for preparing a suspended form of a ground decellularized extracellular matrix with a size-controlled structural components, the suspended form not requiring pre-hydration, the method including the following steps:

separating sheets of a purified fibrous extracellular matrix;

grinding the sheets to prepare a fine powder from the particles of the purified extracellular matrix, followed by fractionation of the powder to obtain a fraction of particles with a required size;

suspending the selected particulate fraction of the purified extracellular matrix in a liquid medium by alternating cycles of stirring with cycles of dispersing particles in a liquid medium, the stirring process being predominant in time, at a temperature that does not cause denaturation of collagen, degassing the resulting suspension of particles.

The size of the structural components of the extracellular matrix in the suspended form is determined by the defibration degree of collagen fiber bundles that can vary from completely intact bundles to smaller bundles and fibers and, according to the proposed method, can be controlled by varying the duration of the stirring and dispersing processes, as well as by the number of alternating cycles, depending on the type of a purified matrix used.

In specific embodiments of the present invention, the extracellular matrix is derived from allogeneic or xenogeneic connective tissues.

In specific embodiments of the present invention, an immersion device or circulation device is used as a homogenizer-disperser.

In another specific embodiment of the present invention, the liquid medium, in which the stirring and dispersing occur, is an isotonic or hypertonic solution that may further comprise at least one component selected from the group comprising growth factors, morphogenetic proteins, hormones, natural therapeutic polysaccharides, and therapeutic substances and drugs, such as antibiotic, hemostatic, analgesic and local anesthetic agents.

In one more specific embodiment of the present invention, all steps are performed under aseptic conditions to provide sterility of the resulting suspension.

Another specific embodiment of the present invention further comprises radiation sterilization of the resulting suspension in a final package, which provides sterility of the resulting suspension.

In one more specific embodiment of the present invention, the grinding of sheets to prepare a fine powder is performed at room temperature.

In another specific embodiment of the present invention, before grinding, the decellularized extracellular matrix is further treated with cross-linking agents.

Another object of the invention is a product prepared by the above-mentioned method that is intended to stimulate reparative tissue regeneration, in particular, to heal skin wounds.

DETAILED DESCRIPTION OF THE INVENTION

Figure 1:
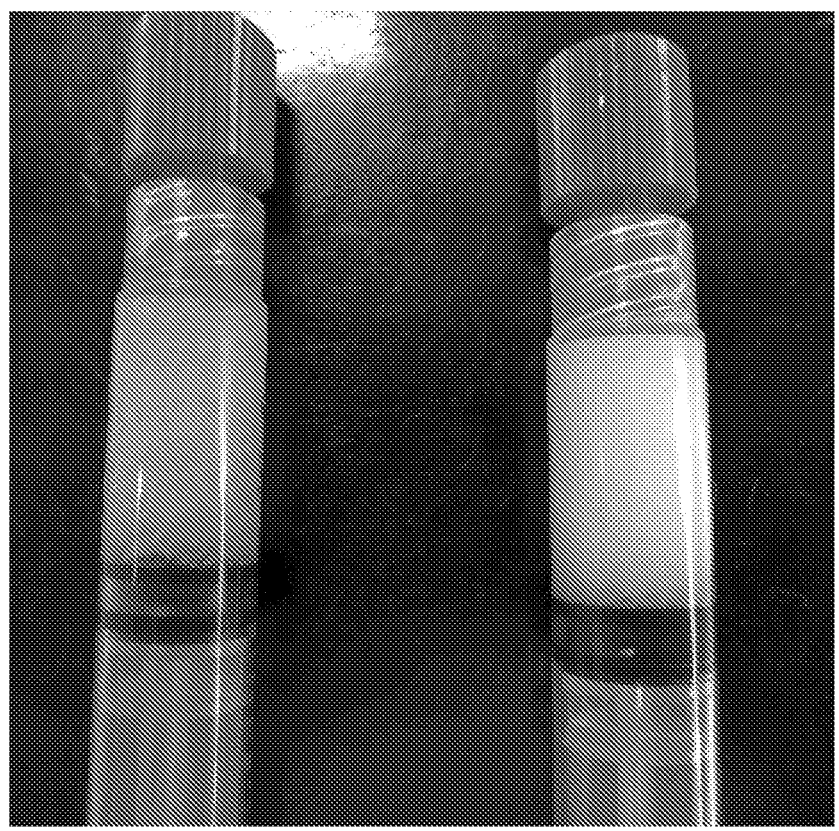
FIG. 1 shows the appearance of syringes with suspensions of the hydrated ground decellularized extracellular matrix of bovine dermis obtained by single dispersion for 60 seconds (left) and 10 minutes (right).

Suspension dosage forms for medical application are prepared from a decellularized extracellular matrix predominantly composed of fibrous proteins (collagen and elastin). The matrix may be prepared both by a patented method (for example, according to RU 2353397 or U.S. Pat. No. 5,336,616 A), and by a method or a combination of methods disclosed in scientific literature (Badylak S. F., Taylor D., Uygun K. Whole-organ tissue engineering: decellularization and recellularization of three-dimensional matrix scaffolds. Annual review of biomedical engineering. 2011, v. 15, No. 13, pp. 27-53). The processes of purification based on the treatment with alkaline solutions are preferred. In addition, it is preferable when the used purification method provides a residual amount of DNAs in the resulting material of less than 50 ng/mg dry weight. The source of the purified extracellular matrix should be allogeneic or xenogeneic connective tissues. An extracellular matrix of the reticular dermis is most suitable for preparing a suspended form. However, the matrix derived from the connective tissue of the pericardium, peritoneum, large-vessel walls, intestine and other organs may be used for this purpose, as well. The decellularized matrix may be preliminary treated with cross-linked agents (for example, soluble carbodiimide orglutaraldehyde) to increase its resistance to biodegradation.

The resultant decellularized extracellular matrix is divided into sheets. The width of the sheets is selected depending on the convenience of their subsequent introduction into a grinder. Then the sheets are dried in air or by lyophilization process to reduce the mechanical resistance of the material and to prevent its local deformation during grinding.

After the drying is complete, the resulting material is ground, preferably at room temperature (in a range of +15 to +25° C.). The grinding is performed by using a mill for grinding of dried fibrous materials of low or medium hardness (for example, PULVERISETTE 15 (FRITSCH, Germany)). It is preferable that a screen insert with a variable hole size is provided for in the device design. This insert makes it possible to change the size distribution of the resulting matrix particles by varying the hole diameter. After grinding, the matrix is a fine powder with a particle size of 5 to 4000 μm.

The size of the particles constituting the solid dispersed phase of the suspension largely determines its rheological and biological properties. As a rule, for intradermal injection through small-diameter needles (30 G, 27 G) used in cosmetology procedures, it is expedient to use suspensions with particles having a size of from 5 to 400 μm. However, for injection of suspensions through large-diameter needles used in surgery, it is more preferable to use fractions of particles with a diameter of 400 to 800 μm. In turn, for external applications that do not require injections, suspensions of particles with a diameter of 700 to 1000 μm are most suitable. In addition, suspensions with larger particles tend to have a longer biodegradation time. In this connection, for the subsequent preparation of suspended forms of a ground decellularized extracellular matrix, the latter is subjected to fractionation to obtain particles of a required size. For this purpose, microscreening is performed in a vibratory sieve shaker (for example, ANALYSETTE 3 PRO (FRITSCH, Germany)) with a set of woven or micro-precision sieves with holes of a required size, used for dry sieving. Sieves used in clean production are to be made in accordance with ISO-3310-1. In microscreening, it is preferable that the sieving process was performed at the vibration amplitude in the range of 0.2 to 2.5 mm. This reduces the loss of material caused by its settling on the walls of the device during dusting. It is also possible to apply special modes of separating particles of a certain size, if provided by the design and software of a device.

The extracellular matrix resulting from grinding and fractionation is used for the further preparation of suspensions. For this purpose, a selected fraction of particles is mixed with a liquid phase of the suspension in a homogenizer-disperser, followed by dispersion. The liquid phase is preferably an isotonic (for example, a 0.9% sodium chloride solution or a 5% glucose solution) or hypertonic (for example, a 10% glucose solution) solution. For improving therapeutic properties of the suspended form, the composition of a liquid dispersion medium can be supplemented with various additional components, such as growth factors, morphogenetic proteins, hormones, therapeutic substances and drugs, in particular antibiotic, hemostatic, analgesic, and local anesthetic agents, as well as natural therapeutic polysaccharides (for example, hyaluronic acid), and a combination of such components.

The homogenizer-disperser may be an immersion device (for example, ULTRA-TURRAX (IKA, Germany) or circulation device (for example, magic LAB (IKA, Germany). When using an immersion disperser, the stirring and dispersing of the components is carried out in a laboratory vessel, for example a glass beaker, and in the reservoir of a device when using a circulation disperser. In both cases, throughout the process of preparing suspension, it is necessary to control its temperature that increases by heating due to friction of the material against the parts of the dispersing module. It is desirable to avoid exceeding the temperature of the suspension above the irreversible denaturation temperature of the main proteins of the used decellularized extracellular matrix. Circulation dispersers can be equipped with additional thermostatically controlled modules, both cooling and heating. These modules can be combined in different parts of the device, creating an optimal temperature mode. For example, a module cooling to 4° C. can be installed on the dispersing module to minimize local heating, and a module heating to 27° C. can be installed on the reservoir jacket to maintain the rheological parameters of the mixture within the operating viscosity parameters of the system.

In the first step of preparing a suspension, a part of the volume of a liquid phase is introduced into a container or reservoir. Then, a stirring module is placed there, for example, an anchor-type mixer. After that, a required amount of a ground decellularized extracellular matrix is gradually manually introduced. Then the remaining calculated volume of the liquid phase is introduced, and the mixer is turned on. A preferable speed of rotation is 20 to 45 rpm. The circulation device can also comprise a special module for automated gradual introduction of a solid dispersed phase, installed thereon. If the mixer power is not enough to evenly mix the suspension, it can be additionally mixed by hand with a stick or another laboratory tool. After completion of the mixing, the dispersing module is immersed in the vessel or reservoir, presetting the maximum gap between the rotor and the stator. The gap in a range of 0.6 to 2 mm is most preferred. The value of torque must be set in advance (for example, 3000-6000 rpm), and then the dispersing module is turned on.

During the preparation of a suspended form, the stirring cycles must be alternated with dispersing cycles, the stirring process being significantly predominant in time. The stirring process must precede the first dispersing process, which ensures the necessary hydration of the ground matrix. By varying the duration of the stirring and dispersing cycles, it is possible to control the defibration degree of the collagen fiber bundles in the ground purified fibrous extracellular matrix. This provides suspensions with different rheological and biological properties. Thus, suspensions with a greater defibration degree will be able to pass through needles of a smaller diameter, and also have a higher biodegradation rate. Suspensions consisting of particles formed by fragments of intact bundles of collagen fibers are obtained when the duration of the stirring cycles is from 10 min to 4 hours and the duration of the dispersing cycles is from 30 seconds to 10 minutes. For the preparation of the suspended forms whose predominant component is bundles of collagen fibers of a smaller order, the duration of the dispersing cycle is from 1 to 60 minutes, while the time of the stirring cycle remains the same. The duration of the dispersing cycle is selected depending on the weight fraction of the solid dispersed phase: the preparation of suspension with a larger concentration of a decellularized matrix requires, as a rule, a longer dispersing cycle. The number of stirring-dispersing cycles must be adjusted empirically depending on the type of the purified matrix used in the work. For matrices prepared by "hard" purification (for example, with alkaline solutions), one stirring-dispersing cycle is usually enough. At the same time, for samples prepared by "mild" method (for example, by treating with detergents), a more number of repeat cycles is required.

Before packing, the resulting suspension is degassed by using vacuum degassing system upon stirring (for example, using a vacuum pump included as standard in a process plant Magic Plant (IKA, Germany)). If the suspension has been prepared by using an immersion homogenizer-disperser, it must be transferred into the reservoir of a degasser. If the suspension has been prepared by using a circulation homogenizer-disperser, it either can be transferred into the reservoir of a degasser or a special degassing module can be used usually provided for by a manufacturer as an additional component of the device.

After degassing, the suspension is packed in a final package (for example, syringes or tubes) manually or by using industrial packing units.

To ensure the sterility of the obtained product, the production process is preferably carried out under aseptic conditions, in accordance with GOST R 52249 and GOST R ISO 13408. In addition, the suspension can be sterilized in the final package by using radiation, if the degradation of the product components under exposure to the radiation does not have a significant effect on the therapeutic properties.

FIELD OF APPLICATION

The suspended forms of a hydrated ground decellularized extracellular matrix, produced by the method described in the present invention can be used in the field of:

(1) dermatology and cosmetology, for the treatment of acute and chronic skin wounds, and correction of atrophic scars and wrinkles;

(2) urology, for the treatment of urinary incontinence and vesicoureteral reflux;

(3) otolaryngology, in plastic surgery of the vocal cords;

(4) reconstructive surgery, for mechanical replacement of defects in various tissues.

The suspended form prepared according to the present invention also can be used as a hemostatic agent and a substrate for cell transplantation in tissue engineering.

The matrix suspensions prepared according to the method disclosed in the present invention can be administered to a desired region both by injection or by surface application, or by a combination of methods. They also can be applied to fixing bandages or other medical products.

EXAMPLE

Sheets of a decellularized extracellular matrix of bovine dermis with an area of 400-700 $cm^2$ were obtained by the method of purification described in RU 2353397. The residual DNA content in the material was 6.5 ng/mg dry weight, which, according to the literature, indicates that cellular components were effectively removed (Crapo P. M., Gilbert T. W., Badylak S. F. An overview of tissue and whole organ decellularization processes. Biomaterials. 2011, v. 32, No. 12, pp. 3233-3243). These layers were cut and dried in air to a residual moisture content of 30%. Then, they were ground with a PULVERISETTE 15 cutting mill (FRITSCH, Germany) comprising an installed sieve insert with a hole size of 500 μm. The resulting fine powder of the purified matrix was subjected to microscreening in a vibratory sieve shaker, ANALYSETTE 3 PRO (FRITSCH, Germany), with a set of micro-precision sieves for dry sieving, with a hole size of 100, 250, 400, 500, or 1000 microns. Upon fractionation, the vibration amplitude was changed during the sieving process in the range from 0.2 mm to 2.5 mm. For further preparation of suspension, a powder fraction was selected that has a particle size of 200-300 μm. A suspended form of the hydrated ground matrix was prepared by using a magic LAB circulation homogenizer-disperser (IKA, Germany). A liquid dispersion medium, which was a 10% glucose solution, in an amount of 200 ml was poured into the reservoir of the device. An anchor-type mixer was then turned on, with a preset rotation speed of 20 rpm. Then, 70 g of the ground matrix and 800 ml of a glucose solution were added to the reservoir, and the resulting suspension was stirred for 40 minutes. At the end of this time, the stirring was stopped, and a dispersing module cooling to 4° C. was switched on, with a preset gap between the rotor and the stator of 1 mm. The form containing particles of intact collagen fiber bundles was prepared by stirring for 15 minutes, and then by dispersing at 3000 rpm for 60 seconds. In turn, the form consisting of collagen fiber bundles with a diameter of 10-20 μm was prepared by treating another batch of matrix particles of the same size in a similar manner, except for the time of the dispersing process. In this case, the suspension was dispersed for 10 minutes. Until the material was present in the reservoir of the device, the temperature of the suspension was monitored using built-in thermometer. The temperature of samples was in the range of 20 to 40 lC.

Then, the suspensions were degassed in the disperser chamber by using a vacuum pump included as standard in a process plant Magic Plant (IKA, Germany). After that, the suspended forms were manually packed under aseptic conditions in Luer lock polypropylene syringes with a volume of 1.5 ml. The syringes were closed with a stopper "Combi-stopper" (B. Braun, Germany) and packed in a roll for sterilization (steriCLIN, Germany). Then they were subjected to radiation sterilization at a dose of 11 kGy.

The obtained products were opaque viscous white suspensions packed in syringes with a plug, as shown in FIG. 1. The suspensions obtained by dispersing for 60 seconds comprised discernible individual particles, while the suspensions dispersed for 10 minutes were homogeneous.

The structure of the obtained samples was analyzed by studying their morphology with light microscopy. For light microscopic examination, preparations of suspensions were prepared by placing 50 μl of a sample between the slide and cover slip. The obtained preparations were analyzed with a NikonNi-U microscope (Nikon, Japan) using a Nikon Plan Fluor 10×/0.3 lens (Nikon, Japan) by the differential interference contrast (DIC) method.

Figure 2:
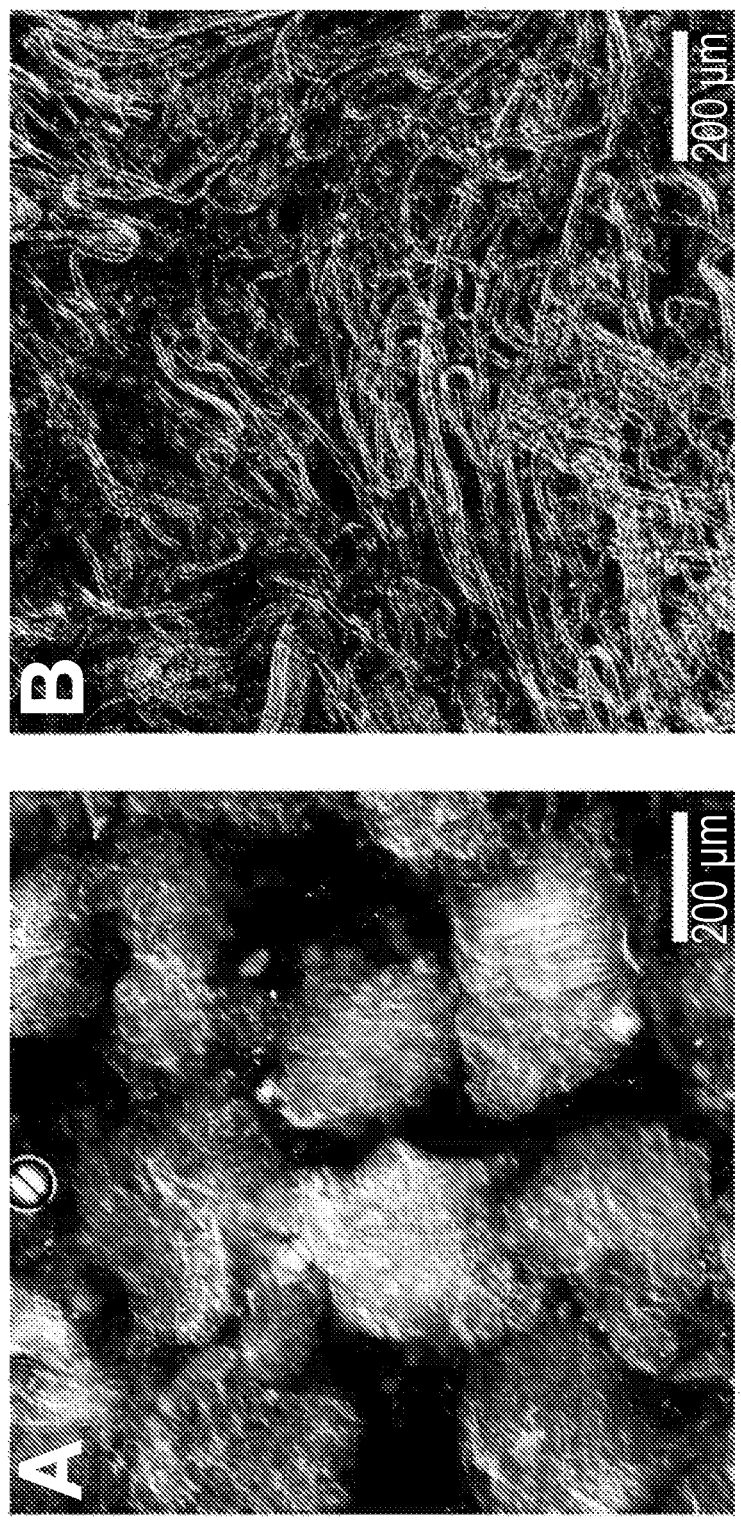
FIG. 2 shows the microscopic structure of suspensions of the hydrated ground decellularized extracellular matrix of bovine dermis obtained by single dispersion for 60 seconds (A) and 10 minutes (B). Light microscopy. Differential interference contrast.

Light microscopic examination showed that the obtained samples consisted of a liquid dispersion medium with fragments of the ground purified fibrous matrix immersed therein (see FIG. 2). In samples of the suspensions dispersed for 60 seconds, these fragments were represented by individual particles of 200-300 μm in size, consisting of tightly stacked bundles of collagen fibers. At the same time, the solid dispersed phase of samples of the suspensions dispersed for 10 minutes was an intertwining network of collagen fiber bundles with a diameter of preferably 10 to 20 ≈m.

The biological effect of the obtained medical devices was assessed by studying their biodegradation and reparative properties in mice on models of subcutaneous implantation and the healing of full-thickness skin wounds, respectively. To analyze the process of biodegradation, mice were injected subcutaneously with 250 μl suspensions in the scapular region through a 24 G needle. Mice of the control group received the same volume of a 10% glucose solution, which is a liquid phase of the medical device. On Day 1 and 5 after injections, mice were euthanized, and skin flaps were excised from the region of the sample injection, the regional lymph nodes also were excised for histological examination. The presence of implants in the injection zone, as well as pathological changes in the tissues surrounding injection point and in the regional lymph nodes were qualitatively assessed.

To study reparative properties, full-thickness skin wounds with a diameter of 0.7 cm were surgically made on the interscapular area of the mice under the anesthesia with Zoletil (Virbac, France, 40 mg/kg body weight). Immediately after wounding, the wounds of the animals of the test groups were completely filled with appropriate suspensions and covered with a fixing bandage "Hydrofilm" (Paul Hartmann, Germany). In turn, the wounds of the control animals were covered directly by a fixing bandage. Immediately after operations and also before the euthanazia, digital macrophotographs of the wounds were made for subsequent photoplanimetric analysis. The animals were euthanized, and the tissues were collected on Day 7 of healing. The obtained tissues were subjected to histological examination. The histological sections were morphometrically evaluated for the epithelization degree of the wound surface and the area of the granulation tissue.

Figure 3:
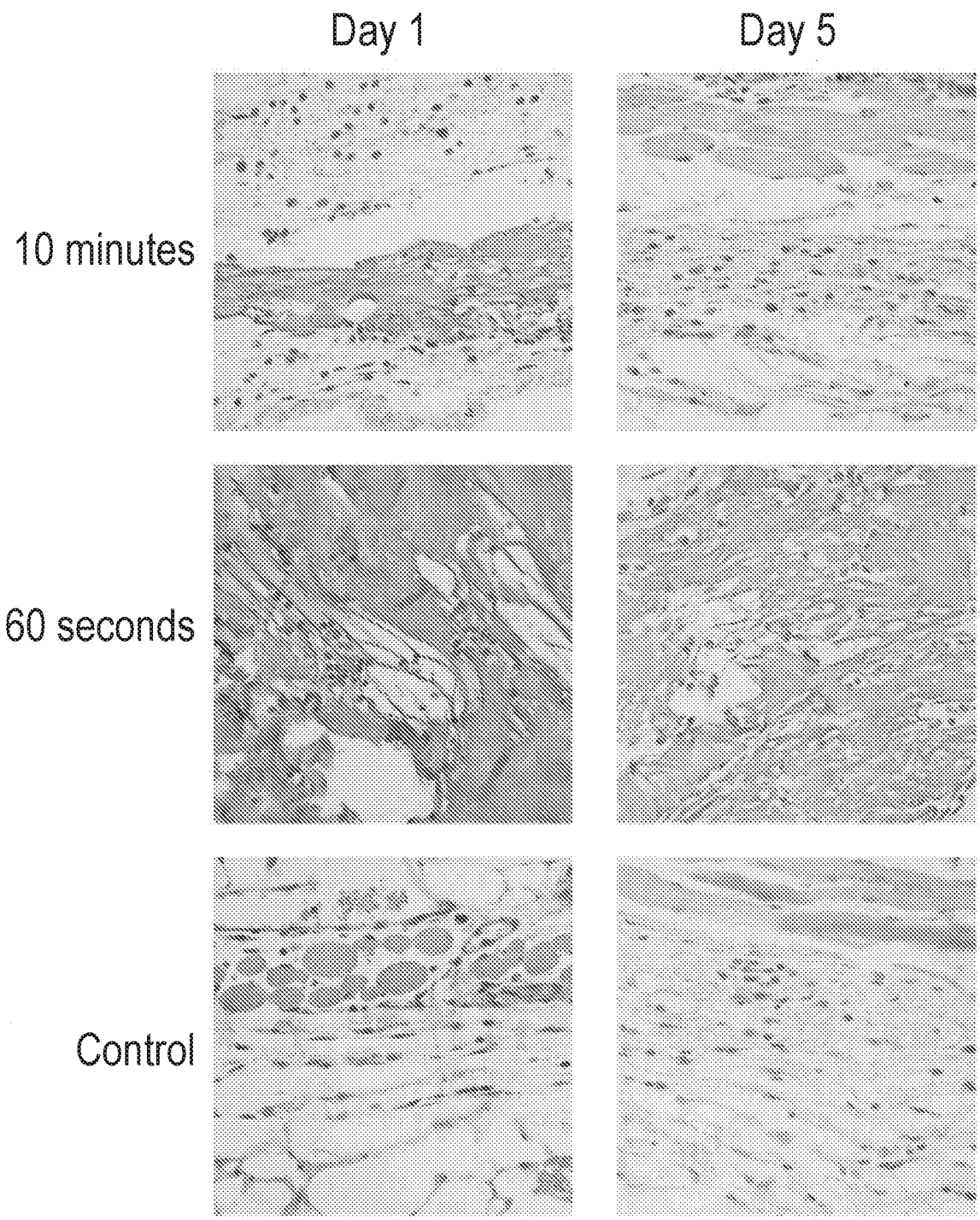
FIG. 3 shows sites of histological sections of tissues injected with suspensions of the hydrated ground decellularized extracellular matrix of bovine dermis obtained by single dispersion for 60 seconds and 10 minutes, and with a 10% glucose solution (control). The sections are stained with hematoxylin and eosin. Representative photomicrographs are shown.

The results of the study in the model of subcutaneous implantation showed a significant difference in the rate of biodegradation of the suspensions. Thus, samples obtained by dispersing for 60 seconds were detected in the injection zones in all animals on both studied time points. At the same time, fragments of the suspension resulting from the 10-minute dispersion were found only in 50% of the animals on Day 1 after the administration. On Day 5 these samples were completely resorbed (see Table 1 and FIG. 3).

TABLE 1

Dynamics of biodegradation of the suspensions according to the data of histological examination

| Method for preparing a suspension | Number of animals with implant fragments discernible in histological sections/total number of animals (the proportion of animals with discernible implant fragments, %) | |
|---|---|---|
| Dispersion, 60 sec | 6/6 (100%) | 6/6 (100%) |
| Dispersion, 10 min | 3/6 (50%) | 0/6 (0%) |

The qualitative morphological study has shown that the administration of both types of suspensions causes the development of a weakly pronounced edema in the surrounding connective tissue, which almost completely dissipates to Day 5 of the experiment, as well as leukocyte infiltration of the injection zone. On both days, Day 1 and Day 5, the predominant cellular form in the infiltrate was monocytes/macrophages. It was found that leukocytes actively penetrated into the material of the implanted samples, which indicates the ability of the medical devices to act as an effective substrate for cell migration. There were no other significant pathological changes in the sites of injections, in particular necrosis, hemorrhages, and fibrosis. The severity of the inflammatory changes in the tissues injected with the suspensions of both types did not significantly exceed the magnitude of the nonspecific tissue reaction induced by the administration of the glucose solution (see FIG. 3). The administration of the samples also did not cause lymphadenitis and other pathological changes in the regional lymph nodes.

Figure 4:
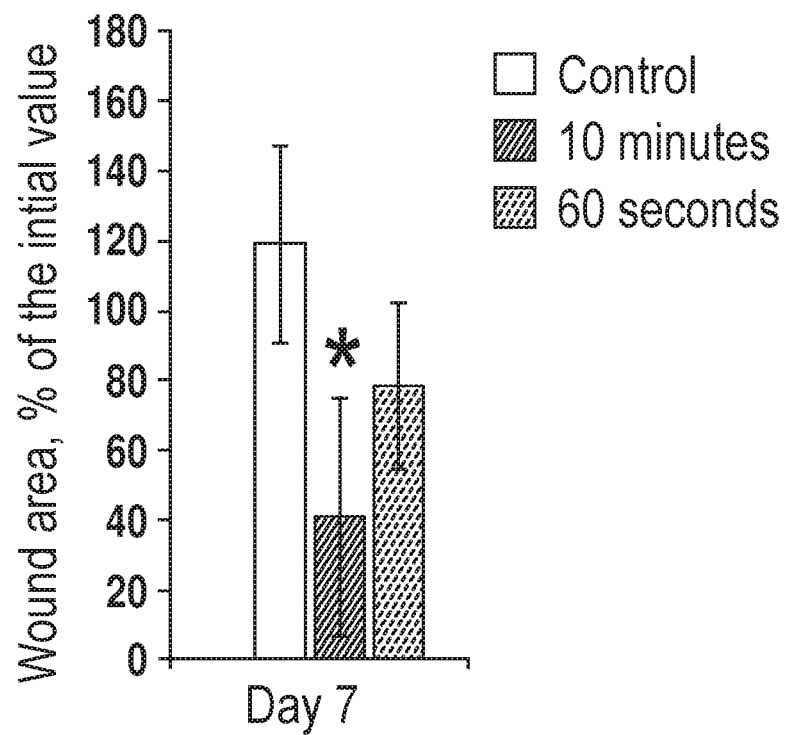
FIG. 4 shows the relative area of wound surfaces in animals whose wounds were healing under dressings comprising suspensions of the hydrated ground decellularized extracellular matrix of bovine dermis obtained by single dispersion for 60 seconds and 10 minutes, and under a fixing bandage without suspension (control). The value marked with an asterisk is statistically significantly ($p<0.05$) differs from the value of the control group.
Figure 5:
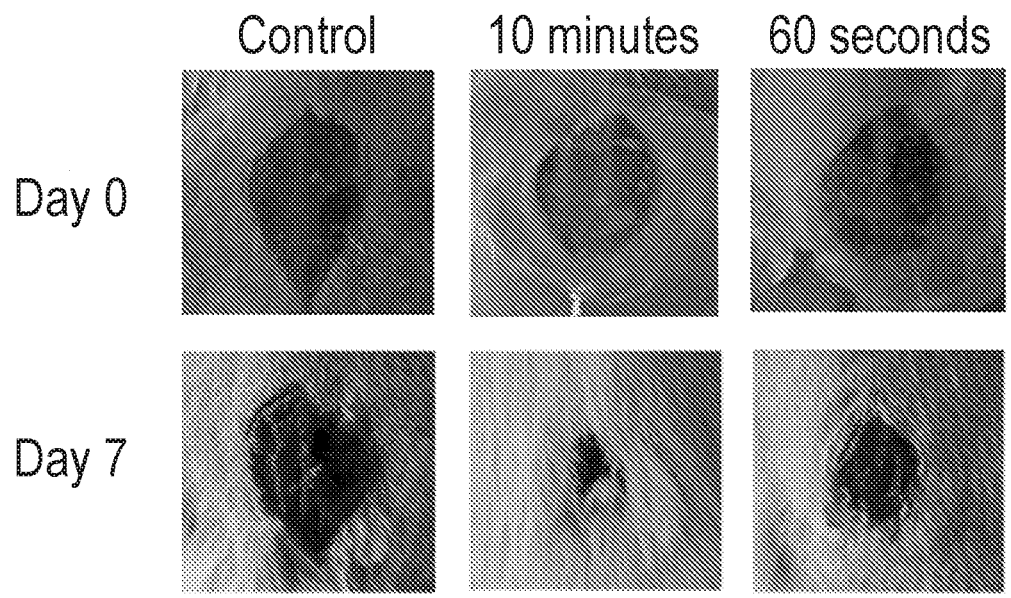
FIG. 5 shows representative photomicrographs of wound surfaces in animals whose wounds were healing under dressings comprising suspensions of the hydrated ground decellularized extracellular matrix of bovine dermis obtained by single dispersion for 60 seconds and 10 minutes, and under a fixing bandage without suspension (control).
Figure 6:
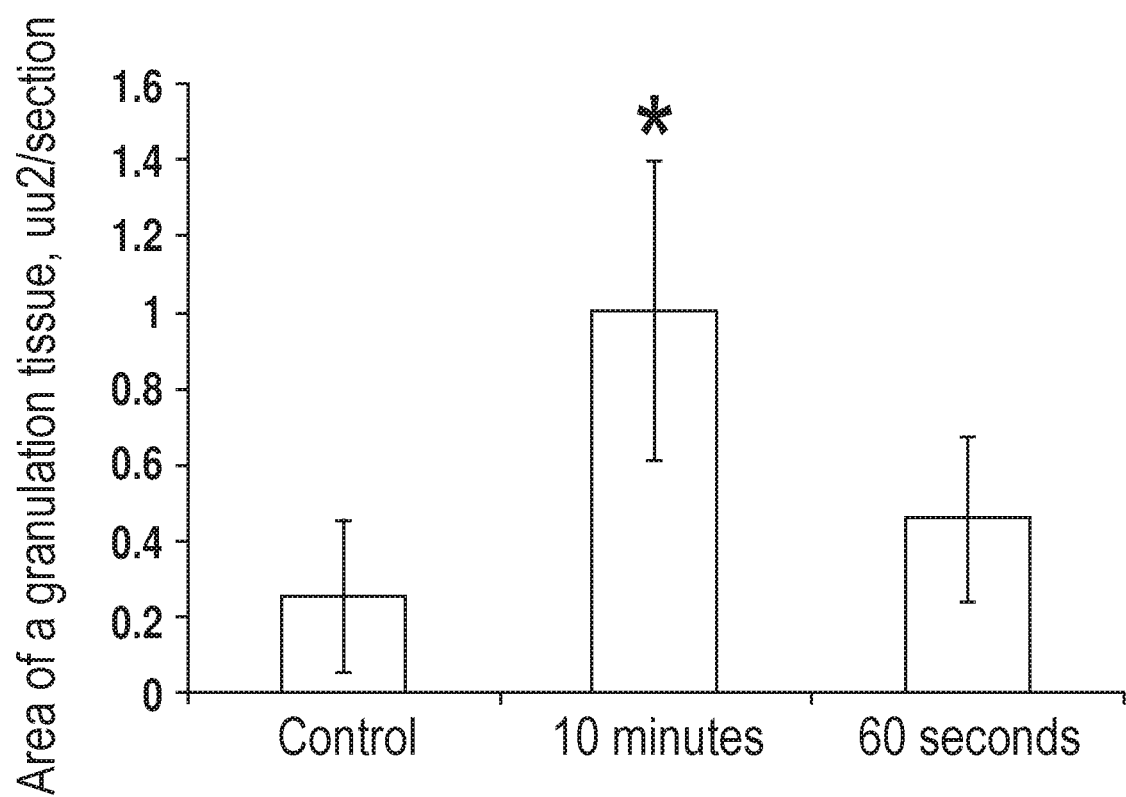
FIG. 6 shows the area of a granulation tissue in histological sections from the central region of a wound in animals whose wounds were healing under dressings comprising suspensions of the hydrated ground decellularized extracellular matrix of bovine dermis obtained by single dispersion for 60 seconds and 10 minutes, and under a fixing bandage without suspension (control). The value marked with an asterisk is statistically significantly ($p<0.05$) differs from the value of the control group.

The study of the reparative properties of the resulting suspensions in the model of healing of a full-thickness skin wound showed a more than two-fold statistically significant decrease in the wound surface area in the animals whose wounds were treated with the suspension dispersed for 10 minutes compared to the control (see FIGS. 4 and 5). The average value of this indicator in the group receiving the suspension dispersed for 60 sec was also lower than in the control, but the magnitude of the effect was not so pronounced (see FIG. 4). The healing of the wounds under the dressings in the form of the suspension dispersed for 10 minutes resulted in a significant, four-fold increase in the amount of granulation tissue in the wound defect area (see FIG. 6). At the same time, the application of the suspension dispersed for 60 seconds onto the wounds increased the value of this indicator on average by less than two times (see FIG. 6). The results of the experiments demonstrate that the time of the dispersing process has an effect on the properties of the obtained suspensions. Thus, the structure (see FIG. 2) of the suspension dispersed for 60 seconds provides a longer time for its resorption, compared to the suspension dispersed for 10 minutes. On the other hand, the suspension dispersed for 10 minutes much more effectively promotes the process of reparative skin regeneration.

The invention claimed is:

1. A method for preparing a suspended form of a ground decellularized extracellular matrix, the suspended form not requiring pre-hydration, the method comprising:
    separating sheets of a purified fibrous extracellular matrix,
        grinding the sheets to prepare a fine powder from the particles of the purified extracellular matrix,
    fractionation of the powder, and
    suspending the selected particulate fraction of the purified extracellular matrix in a liquid medium by first stirring the selected particulate fraction in the liquid medium and then dispersing the stirred selected particulate fraction in the liquid medium for 10 mins at 3000 rpm under a temperature in the range of 20 to 40° C., and degassing the resulting particulate suspension.

2. The method of claim 1, wherein the extracellular matrix is derived from bovine dermis.

3. The method of claim 1, wherein a homogenizer-disperser is a circulation device.

4. The method of claim 1, wherein the liquid medium, in which the stirring and dispersing are performed, is a hypertonic solution.

5. The method of claim 1, further comprising radiation sterilization of the resulting suspension in a final package to provide sterility of the resulting suspended form.

6. The method of claim 1, wherein the grinding of sheets to prepare a fine powder is carried out at room temperature.

* * * * *